United States Patent
Wyatt et al.

(10) Patent No.: US 8,360,244 B2
(45) Date of Patent: Jan. 29, 2013

(54) METHOD AND APPARATUS FOR OPTIMIZING THE SEPARATION OF SMALL PARTICLES USING THE ASYMMETRIC FLOW FIELD FLOW FRACTIONATION METHOD

(75) Inventors: Philip J. Wyatt, Santa Barbra, CA (US); Michelle H. Chen, Goleta, CA (US); David N. Villalpando, Lompoc, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 942 days.

(21) Appl. No.: 12/157,367

(22) Filed: Jun. 9, 2008

(65) Prior Publication Data

US 2009/0301942 A1    Dec. 10, 2009

(51) Int. Cl.
   *B03B 5/60*    (2006.01)
(52) U.S. Cl. .................. 209/156; 209/250; 210/321.84; 210/650; 210/748.01; 422/63; 422/503; 422/535; 436/53; 436/176
(58) Field of Classification Search .................. 209/18, 209/156, 250; 210/321.84, 650, 748.01; 422/63, 503, 513, 527, 537, 535; 436/53, 436/178
See application file for complete search history.

(56) References Cited

U.S. PATENT DOCUMENTS

| | | | |
|---|---|---|---|
| 5,240,618 A * | 8/1993 | Caldwell et al. | 73/863.21 |
| 6,180,906 B1 * | 1/2001 | Trainoff | 209/127.1 |
| 6,365,050 B1 | 4/2002 | Cauchon | |
| 6,562,307 B1 | 5/2003 | Schuch et al. | |
| 6,607,655 B1 * | 8/2003 | Lowe et al. | 205/334 |
| 2008/0003689 A1 | 1/2008 | Lee et al. | |
| 2008/0087584 A1 * | 4/2008 | Johnson et al. | 209/606 |

FOREIGN PATENT DOCUMENTS

JP    2001-059838    3/2001

OTHER PUBLICATIONS

A. Litzen, Separation speed, retention, and dispersion in asymmetrical flow field-flow fractionation as functions of channel dimensions and flow rates, Analytical Biochemistry, 1993, pp. 461-470, V. 65, Academic Press Inc., New York.

K. G. Wahlund, Et.Al., Application of an asymmetrical flow field-flow fractionation channel to the separation and characterization of proteins, plasmids, plasmid fragments, polysacharides and unicellular algae, J. Chromatography, 1989, pp. 73-87, V. 461, Elsevier Science Publishers B.V., Amsterdam.

C. Tank, Et.Al., Characterization of water-soluble polymers and aqueous colloids with asymmetrical flow field-flow fractionation, Macromolecular Chemistry and Physics, 1996, pp. 2943-2959, V. 197, Wiley-Vch Verlag, Weinheim.

M. H. Moon, Et.Al., Effect of inlet frit lengths on the hydrodynamic relaxation efficiency in frit inlet asymmetrical flow field-flow fractionation, J. Liquid Chromatography, 2003, pp. 2369-2379, V. 26, Monticello, New York.

(Continued)

*Primary Examiner* — Joseph C Rodriguez
*Assistant Examiner* — Kalyanavenkateshware Kumar
(74) *Attorney, Agent, or Firm* — Philip J. Wyatt; David N. Villalpando

(57) ABSTRACT

A new type of asymmetric flow field flow fractionator, A4F, is described permitting improved sample fractionation means by providing a range of available channel lengths within the same A4F unit. With such an apparatus, samples may be optimally separated by performing such fractionations as a function of channel length. The ability to vary channel length within the same A4F unit has heretofore been unavailable.

19 Claims, 7 Drawing Sheets

OTHER PUBLICATIONS

J. C. Giddings, Field Flow Fractionation: Analysis of Macromolecular, Colloidal, and Particulate Materials, Science, 1993, pp. 1456-1465, V 260, AAAS, USA.

K.-G. Wahlund and J.C. Giddings, Properties of an Asymmetrical Flow Field-Flow Fractionation Channel Having One Permeable Wall, Anal. Chem., 1987, pp. 1332-1339, V 59, ACS, USA.

Wyatt Technology Corporation, The Eclipse promotional literature, 2005, Wyatt Technology Corporation, Goleta, USA.

Fffractionation, Ltd., Instrument Manual for Model F-1000 Universal Fractionator, Instrument manual, 1994, FFFractionation, Ltd., Salt Lake City, USA.

* cited by examiner

METHOD AND APPARATUS FOR OPTIMIZING THE SEPARATION OF SMALL PARTICLES USING THE ASYMMETRIC FLOW FIELD FLOW FRACTIONATION METHOD

BACKGROUND

The need to separate small particles such as macromolecules, virus-like particles, bacteria, or colloids has become an important task preparatory to their characterization in terms of their mass or size and the determinations of the distributions thereof. In recent years, one of the most successful means by which such particles may be separated is by asymmetric flow field flow fractionation, AsFFFF, or A4F for short. The apparatus is a variant of the earlier cross flow FFF device described by J. Calvin Giddings in his 1993 Science paper, volume 260, pages 1456-1465. The A4F variation is described by its inventor Carl-Gustav Wahlund in his 1987 paper with J. Calvin Giddings "Properties of an asymmetrical flow field-flow fractionation channel having one permeable wall," Analytical Chemistry 59, 1332-39.

An A4F unit is comprised of the following elements together with means to hold them together: 1) a bottom assembly structure holding a liquid-permeable frit, usually made from sintered stainless steel particles, 2) a permeable membrane that lies over the frit, 3) a spacer of thickness from about 75 to 800 µm containing a cavity, and 4) a top assembly structure generally holding a transparent plate of material such as Lexan® or glass. The resulting sandwich is held together with bolts or other means. The coffin-shaped cavity in the spacer will serve as the channel in which separation will occur. The top assembly structure contains three holes that pass through the generally transparent plate, called ports, that are centered above the channel and permit the attachments of fittings thereto. These ports are: 1) a mobile phase inlet port located near the beginning of the channel and through which is pumped the carrier liquid, the so-called mobile phase, 2) a sample port, very close to and downstream of the inlet port, into which an aliquot of the sample to be separated is introduced to the channel, and 3) an exit port through which the fractionated aliquot leaves the channel.

A4F channels are used to separate particles of the varying classes listed above and spanning a size range from a few nanometers to tens of micrometers. The separation of a sample aliquot comprised of such particles depends in turn on the length, breadth, and thickness of the coffin-shaped cavity. In addition, it depends on the channel flow rate, the ratio of the cross flow to channel flow, temperature, liquid viscosity, pH, ionicity, the physical composition of the particles themselves, and the type of permeable membrane lying over the frit. By suitably programming the time variation of the channel-to-cross flow ratio, separations of different particle classes may be improved significantly and often a great range of particle sizes present in the injected sample aliquot may be separated in the same run. Indeed, for each class of particles to be separated an optimal separation may be developed by empirically varying those variables accessible. The only variable that cannot be changed for a conventional channel is the channel length.

Historically, the channel length for A4F has been of the order of 25 to 30 cm with a greatest breadth of the order on 1 to 3 cm that tapers along its length and ends at a breadth comparable to the breadth of the exit port. Recent studies have suggested that a channel of shorter length would provide certain benefits and, on this basis, a completely new structure was developed and incorporated into a shorter A4F unit. However, with the choice of a single channel, the possibility of providing better separations for certain classes of particles can never be thoroughly studied unless all the affecting variables listed above may be tested. Thus effects of flow rates on the separation of each class of particle are easily tested using a fixed channel, but current channel design tradition does not allow for varying the length. It does permit variation of channel breadth and membrane thickness with the same three port locations. If only a single channel length is available, several questions arise: Is there a length that will produce better separations than that produced by either of the fixed length devices available? Is there an optimal length that will produce equivalent separations but require smaller sample aliquot size? May one combine the results obtained from several different lengths for the same samples to yield better characterizations of the samples examined? Does optimal separation of each sample type have an associated best channel length?

It is a basic objective of this invention to provide an apparatus and method by which these questions may be answered. Separation depends on many parameters, some of which are controlled by the software and the system operator. Until this invention, however, one parameter, the channel length, could not be varied. Thus it is a further object of the present invention to provide greater separation flexibility by which samples may be characterized more extensively by providing accessibility to different channel lengths within the same channel structure.

BRIEF DESCRIPTION OF THE INVENTION

A new form of the generally transparent top plate element of an A4F unit is described permitting, thereby, the use of spacers providing for a variety of channel lengths and shapes. Rather than provide a single set of three locations for the inlet, sample injection, and exit ports, the top plate form of the present invention includes provision for a plurality of sample injection and exit port locations. A given separation depends significantly upon the distance from the sample injection port to the exit port where the fractionated sample aliquot leaves the channel, i.e. the region of the channel along which the aliquot is being fractionated by the combined actions of the channel and cross flows. For a single channel, therefore, by selecting a sample injection port closer to the exit port through which to inject the sample, the effective length of the channel is shortened; all other structural elements remaining the same. Alternatively, the spacer itself may be replaced with one having a shorter channel. For this modification, the initial sample injection port would remain the same, but a fractionated sample exit port closer to it would be used based on the appropriate location for the new effective channel. Thus by using a shorter spacer channel and selecting an exit port nearer the sample injection port, the channel separation length would be shortened. Until needed, the plurality of unused port apertures remain sealed or blocked.

DETAILED DESCRIPTION OF THE INVENTION

Figure 1:
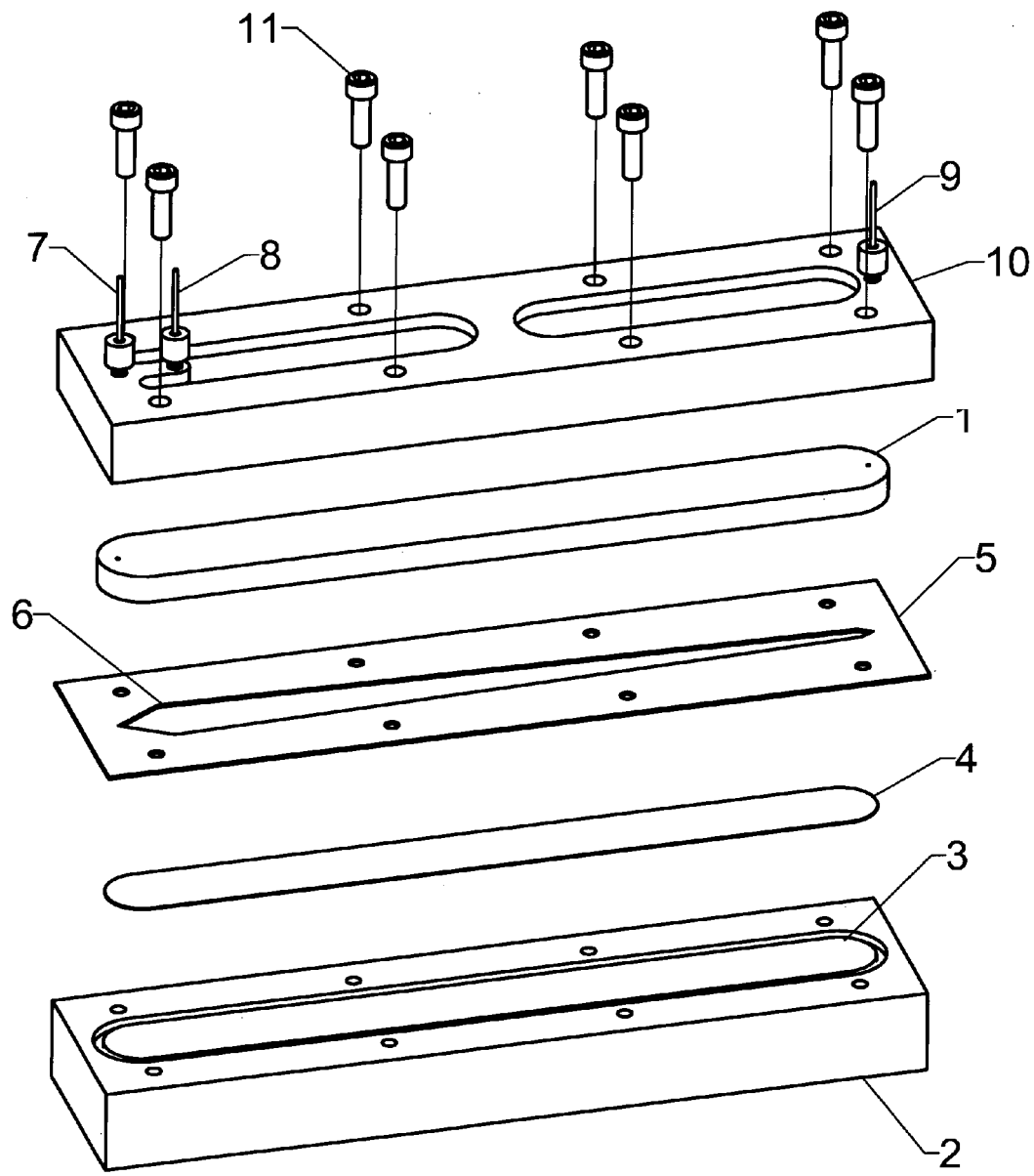
FIG. 1 shows the A4F structural elements of the prior art.

FIG. 1 shows the traditional structure of an asymmetric flow field flow fractionation unit and its components. The typical unit is comprised of a top plate assembly 10 holding a top plate 1, a bottom plate 2 containing the porous frit structure 3, a membrane 4 through which some of the fluid may flow, a spacer 5 in which is cut out a tapered channel 6, an inlet port 7 for the insertion of the mobile phase, a sample injection port 8 through which the sample aliquot to be fractionated is introduced, an exit port 9 through which the fractionated sample and mobile phase will leave the structure prior to entering one or more detection devices, and assorted pumps and controllers to supply adequate flow and control for the device. The top plate assembly 10 is generally secured to the bottom plate 2 by bolts 11. The top plate 1 is generally transparent so that, if needed, the channel 6 may be observed during sample fractionation. It generally also contains the ports 7, 8, and 9. Flow through the exit port 9 is produced by restricting the flow leaving the membrane 4. Thus if the mobile phase inlet flow is, say 2 ml per minute and the flow through the membrane is restricted to 0.5 ml/min, the outlet flow would be 1.5 ml/min.

Once the particles have been separated by the A4F unit, they are generally examined by means of different classes of detection instruments responsive thereto. These may include light-scattering photometers, UV absorption meters, differential refractive index detectors, and differential viscometers. Such devices are used to characterize the separated particles/molecules in terms of their molar mass, intrinsic viscometry, size, etc.

The so-called fractionating power, F, i.e. the ability of the channel to separate particles of different sizes, of such a channel may be expressed by the relation $$F = S\left(\frac{w}{384bLD}\right)\left(\frac{V_{cross}^{3/2}}{V_{channel}^{1/2}}\right), \quad (1)$$

where S is the so-called selectivity constant, $V_{cross}$ the channel cross flow rate, $V_{channel}$ the channel longitudinal flow rate, b is channel breadth, L the channel length, w the channel thickness, and D the particle diffusion coefficient related by the Einstein-Stokes equation to the particle's hydrodynamic radius $R_h$, i.e.

$$R_h = \frac{k_b T}{6\pi \eta D}, \quad (2)$$

where $\eta$ is the solution viscosity at the absolute temperature T, and $k_b$ Boltzmann's constant.

From Eq. (1) above, we note that decreasing the channel length appears to have the potential to improve the separation of a sample. However, the ability of a channel to retain particles depends on the cross flow per unit area of the channel-defined area of the membrane, i.e. the membrane region defined by the cavity in the spacer. Since the cross flow per unit area is approximately $V_{cross}/bL=\xi$, Eq. (1) reduces to $$F = S\frac{w\xi}{384D}\sqrt{\frac{V_{cross}^*}{V_{Channel}}}. \quad (3)$$

Figure 2:
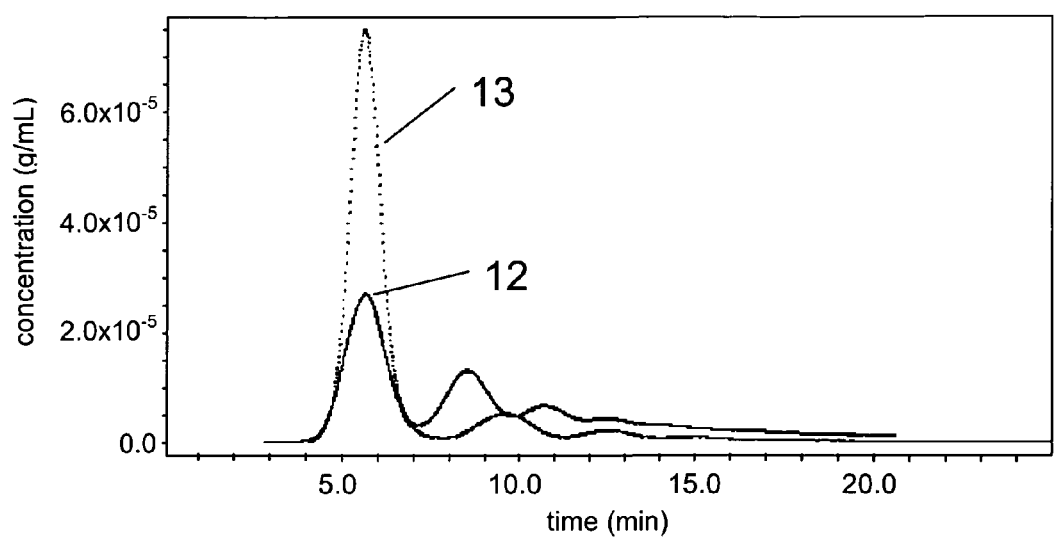
FIG. 2 illustrates differences in fractionation using two different channel lengths.

FIG. 2 shows a comparison of the separation by a standard channel 12 of channel length 25 cm with that of a shorter channel 13 of channel length 18 cm. The spacers into which these cavities were cut were of the same 490 µm thickness. In addition, the cross flows were slightly different as were the corresponding longitudinal flow rates. For the standard and short cavities, the corresponding channel and cross flows were (1, 3.0) ml/min and (0.5, 2.0) respectively. Thus the associated ξ-values were 3/(bL$_t$) and 2/(bL$_s$), respectively. The corresponding ratios of the term $$\sqrt{\frac{V_{cross}}{V_{channel}}}$$

for the standard and smaller channels were 1.73 and 2.00, respectively. From Eq. (3), the ratio of the fractionating power of the short channel to the standard channel is just 1.07. This factor corresponds to an augmented fractionation of a negligible 7%. Nevertheless, for the same amount of injected sample, the shorter channel produced a sharper peak with correspondingly smaller dilution because, for the example shown, the channel flow for the short channel was only half that of the longer channel. With the flexibility of adjusting the two flow rates, the comparison of the two channels using the rates selected does not yield a quantitatively improved fractionating power for the shorter length. Indeed, for the two lengths selected, slight modifications of the cross flow for the longer channel would have produced no difference of their associated fractionating powers. Yet consider the following study comparing channels of two different lengths yielded results shown in the table below:

TABLE 1

| Comparison the standard 25 cm channel with the shorter 18 cm channel | | |
|---|---|---|
| Feature | Standard channel (25 cm) | Shorter channel (18 cm) |
| Time required | 56 minutes | 31 minutes |
| Eluent volume/run | 159 mL | 70 mL |
| Injected sample size | 20 µg | 2.5-10 µg |

Although the types of molecules that were the source of this result were quite different from those producing the data of FIG. 2, it is important to note that the shorter channel appeared to have achieved the same quality of separation yet it was faster and required less sample.

From FIG. 2, we see that the peak arising from the dimer and higher oligomeric fractions are eluting earlier: another confirmation of the observations of Table. 1. Thus, the ability to analyze a particular sample by examining fractionations as a function of channel length would be an invaluable feature of any A4F system. Currently, only a single channel experiment is possible and, from a practical point of view, the determination of a channel length providing an optimal separation may be achieved only by the use of distinct channel-containing units, each of which is based on a fixed length. At the time of this invention, only two different channel structures, with correspondingly different channel lengths, were available and data from them has been similar to that of Table 1, above. Although the shorter channel data 13 of FIG. 2 are suggestive of possible improvement over the longer channel data 12, closer examination of 13 suggests that for the oligomeric states, the peaks do not appear to be baseline resolved. The minima between peaks increase their departure from the baseline with increasing elution. Clearly absent from the data presented are any estimates of the functional dependence of channel length on separation and resolution. With only two channel length values and a relatively crude A4F theory, the importance of changing channel length, with or without variation of the other parameters such as flow rates, remains an unanswered question.

Figure 3:
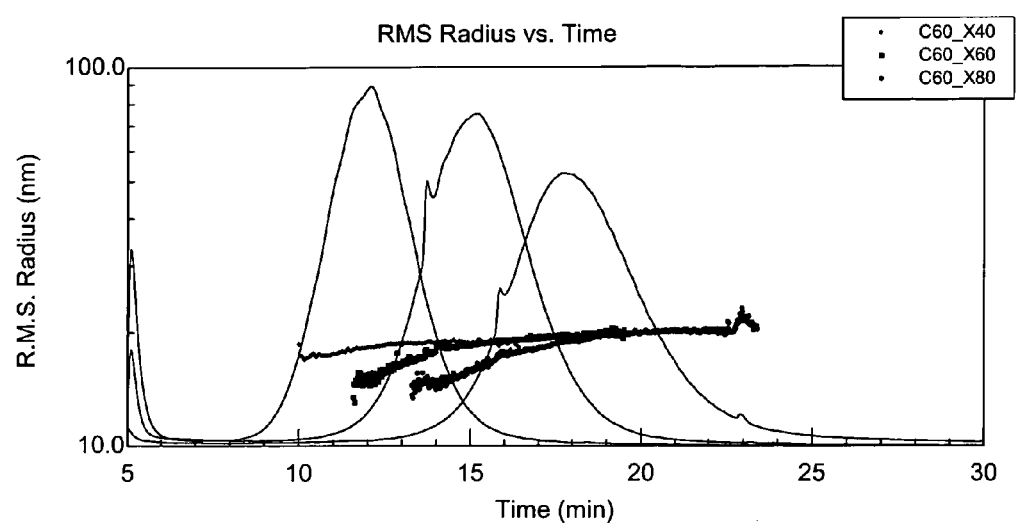
FIG. 3 illustrates the effect of changing the cross flow on a separation where the channel flow is kept constant.

FIG. 3, for example, shows the effect of varying the cross flow on a sample of polystyrene latex spheres of nominal 50 nm diameter when the channel longitudinal flow rate is kept constant at 60 ml/hour. The measured root mean square radius, $<r_g^2>^{1/2} = r_g$, which is proportional to the particles' hydrodynamic radius, $\alpha$, by the relation $r_g = \sqrt{3/5}a$. For the three cross flow rates of 40, 60, and 80 ml/hour, the elutions are effectively equal spanning the same range of sizes. The size distribution deduced from the most rapid elution, occurring at a cross flow of 40 ml/hour, appears truncated at the early elutions due simply to the selection of the interval for calculation of the particle sizes. For some reason, the range selected for actual calculation was smaller for this lowest cross section. The more slowly eluting sample, corresponding to the lowest cross flow of 40 ml/hour, shows signs of the presence of a small peak fraction containing larger size particles. This well may have corresponded to particles retained on the membrane and released only after the cross flow rate was set at zero. Although there is nothing suggestive of a better choice of cross flow, it would have been interesting to see similar results when the sample contained more than a single size, i.e. the importance of a fractionation over a longer time period. Missing completely is a similar comparison using a channel of a different length.

Because there has been no means by which the effects of channel length variation may be examined in detail, only the results of two commercially available structures have been used to examine such consequences. Consider now the structure shown in FIG. 4. Here we see a channel structure identical to that of FIG. 1 except that a plurality of additional sample injection ports is included. A possible set of such additional ports are indicated by labeling with indicia 14, 15, 16, 17, and 18, respectively. The actual number of such ports and their locations along the length of the channel may vary. The distance of each these sample injection ports from the exit port 9 corresponds to the channel's effective fractionation length, i.e. the distance along which the sample may be fractionated before exiting the channel. Thus, corresponding to each such injection port, a corresponding sample injection and sample focusing initiates the subsequent traditional separation. Separating the same sample over a range of the channel lengths, by selecting a range of injection ports for the sequential injection of identical sample aliquots, will permit the determination of an optimal channel length for each sample so studied. Sample injection ports unused during a particular injection may be plugged temporarily or controlled by external valves and tubing. Thus a multi port sample injection valve may be configured so that each injection port has a corresponding location; all ports being connected at once with only one activated at a time. Once automated, measurement of channel behavior as a function of length, channel flow and cross flow rates may be easily performed.

The types of possible experiments discussed above suggest strongly that all current commercially available A4F unit structures have no firm basis for the channel length provided. There are no choices available and scarce data suggesting why the A4F unit has been produced for use only for a channel specified by the vendor. Far too little study has been made of separation benefits associated with a specific channel length. Naturally, there are many studies such as shown in FIG. 3 demonstrating the effects of variations of flow rates, spacer thickness, and spacer shape. Until this invention, however, the effect of channel length has never been a subject for study. It may be possible to associate an optimal length to each distinct sample type. Such studies are long overdue.

Figure 4:
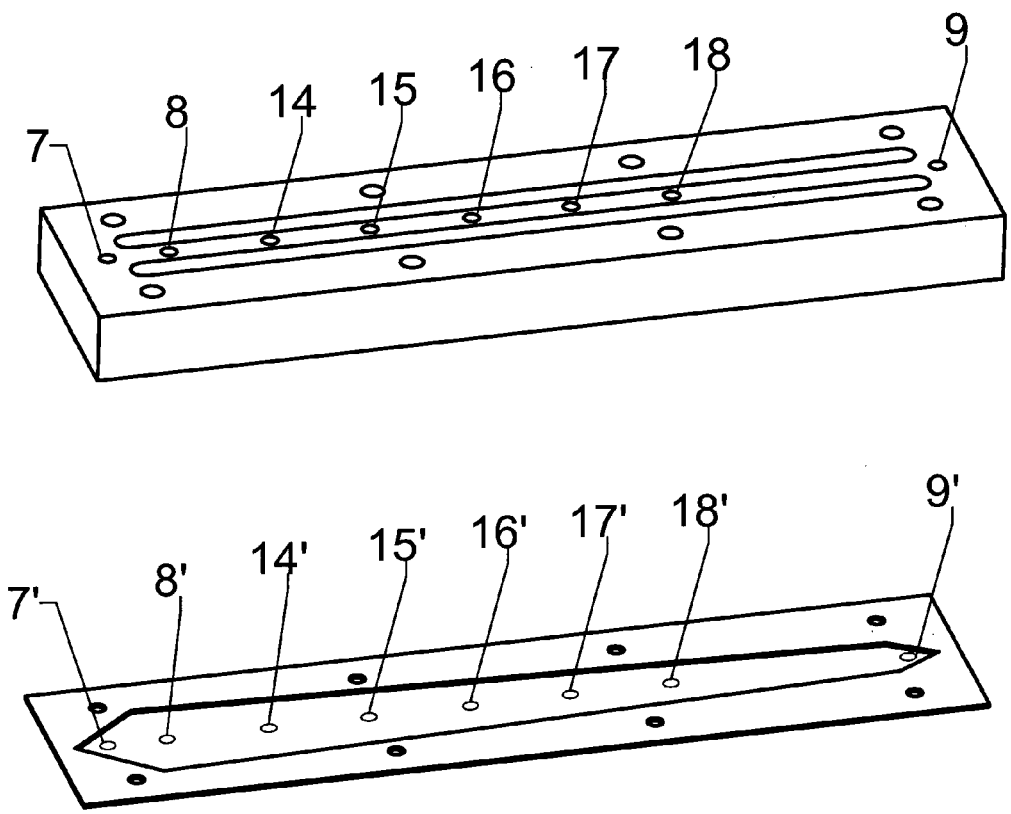
FIG. 4 shows an embodiment of the top plate of the current invention.
Figure 5:
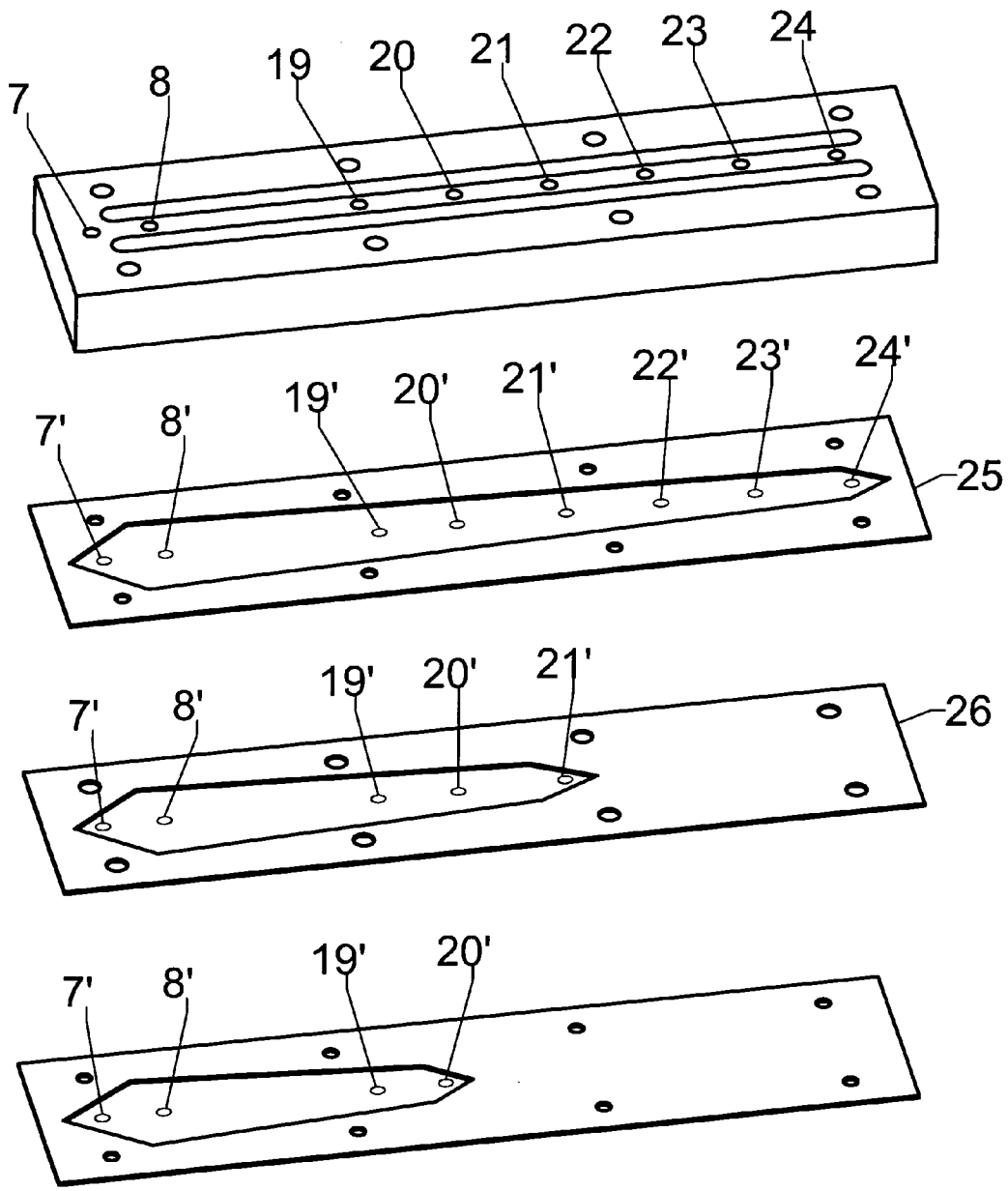
FIG. 5 shows a set of spacers each with a different channel for use with the current invention.

Although the embodiment shown by FIG. 4 would permit further exploration and study of channel length effects, it may prove important to examine channel length effects while maintaining a constant channel shape. The embodiment of FIG. 4 makes use of the same channel shape from the selected injection port to the outlet port. Traditionally, the region between the mobile phase inlet port to the sample injection port is provided with a tapered shape. Using the different sample injection ports of the present invention as shown in FIG. 4 eliminates this transition cavity shape. It is not expected to affect the subsequent separation, though very little comment on or study of such pre-injection shape may be found in the literature. Another embodiment of the invention, useful for such studies, is shown in FIG. 5. For this embodiment, the A4F unit must be opened and the spacer exchanged for each length selected, but similar channel shapes may be used for different selected lengths.

The top plate shown in FIG. 5 shows the top plate structure having mobile phase injection port 7 and sample injection port 8. In addition are a set of outflow ports 19, 20, 21, 22, 23, and 24. Corresponding to each such outlet port would be a spacer with a channel sharing the same inlet and sample injection ports, 7 and 8, Thus, the spacer labeled 25 would have a cavity cut out corresponding to the outlet port 24, the spacer labeled 26 an outlet port 21, etc. The number of such outlet ports, for which there would be an associated channel length is shown in FIG. 5 as six though this number and the distance increments between ports may be greater or fewer.

Figure 6:
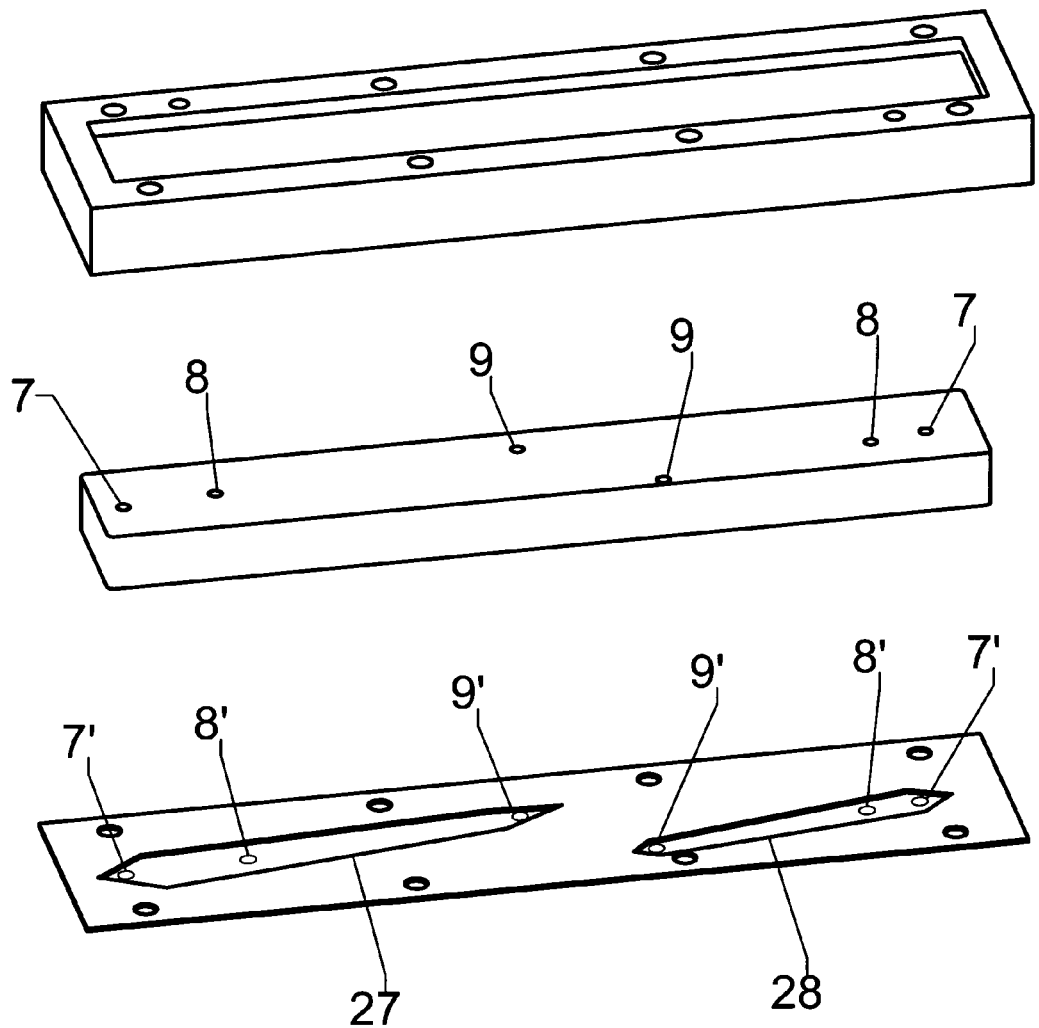
FIG. 6 shows top plate and corresponding spacer for use with two channels.

The flexibility of the top plate and the possibilities for various port locations located therein has been shown via the exemplars of FIGS. 4 and 5. The ability to expand the use of the top plate to accommodate such a plethora of port locations has been, therein, clearly illustrated. Another simple modification is shown in FIG. 6 wherein the top plate has been fitted with ports to permit a single spacer to provide for two or more distinct cavities. For this simple example, the top plate is supplied with 2 sets of mobile phase inlet ports 7 and corresponding 2 sets of sample injection ports 8. The spacer has two corresponding outlet ports 9, though the two cavities 27 and 28 may be of different length and shape. Note that the cavities may be connected to the same controller unit and, by means of appropriate multi-valve structures; such channels may be switched and used sequentially. Modifying the top plate of the A4F channel to include the various ports required to allow additional active cavities within the same spacer has a further benefit: the utility of the membrane, the most expensive disposable required for such separations, may be greatly enhanced. Current designs of the channel structure result in only a small fraction of the membrane surface area being used. By changing the location of the traditional channel to permit the placement of two or more channels within the same spacer, the membrane will be used more effectively and operational costs reduced dramatically.

Figure 7:
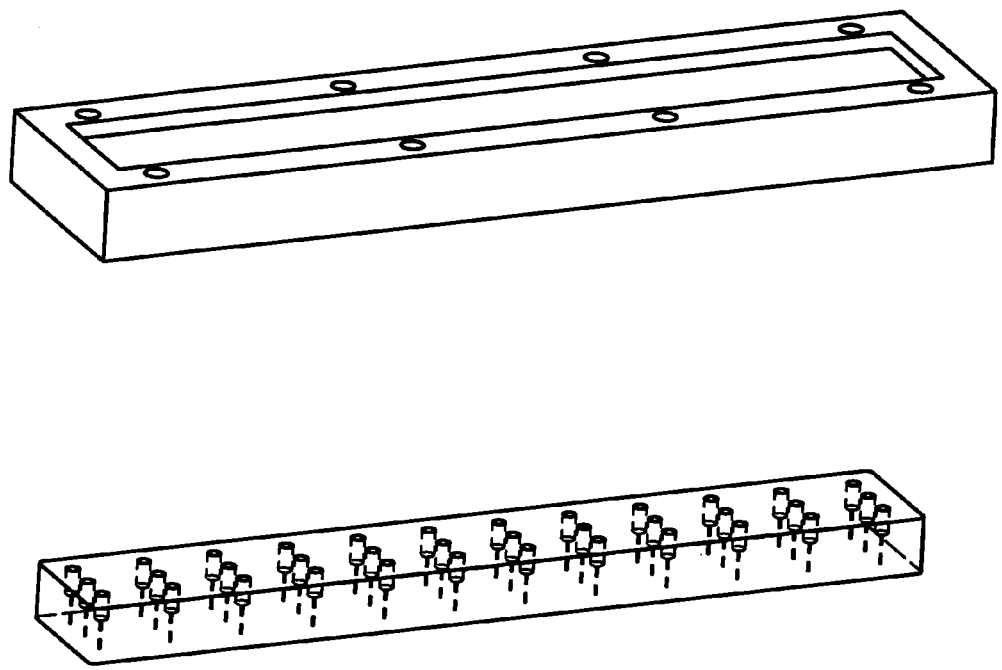
FIG. 7 shows another embodiment of the top plate of the current invention with multiple ports placed therein allowing added flexibility of channel structures selectable by the user

Even greater versatility may be imparted to this multi-channel implementation by adding sufficient additional ports for each channel to permit its implementation similar to the inventive modes described in FIG. 4 or 5. An example of this embodiment, with an array of ports extend over the entire accessible surface of the top plate, is shown in FIG. 7. By accessible is meant regions directly below such apertures must include a spacer into which may be cut a cavity, or part thereof, exposing thereunder a membrane supported by a permeable frit structure. The significance of these inventive elements cannot be overemphasized. Not only do they provide greater flexibility for the A4F technique, but they permit greater utilization of the expensive membrane element. Most importantly, they expand considerably the ability to derive optimal separation conditions for each class of molecule and/or particle.

As will be evident to those skilled in the arts of particle separation and field flow fractionation, there are many obvious variations of the versatile channel implementations and applications we have invented and described that do not depart from the fundamental elements that we have listed for their practice; all such variations are but obvious implementations of our invention described hereinbefore and are included by reference to our claims, which follow.

The invention claimed is:

1. A method to improve the characterization of particles separated by an asymmetric flow field flow fractionation unit, A4F, whose structure comprises
  i. a top plate assembly containing ports,
  ii. a spacer containing two or more cavities separating said top plate assembly from a bottom plate assembly,
  iii. a membrane preventing particles from entering
  iv. a supporting frit structure, and
  v. a bottom plate assembly to which said top plate assembly can be rigidly attached sealing, thereby, said cavity between said membrane and said top plate;
comprising the steps of
  A. assembling a channel structure which provides a plurality of cavities of different cavity configurations by using one spacer containing a plurality of cavities of different cavity configurations therein;
  B. creating a suspension of said particles to be characterized;
  C. injecting an aliquot of said particles into a first cavity configuration of said A4F channel means;
  D. fractionating said injected aliquot by said first cavity configuration;
  E. measuring said fractionated aliquot by detector means;
  F. injecting successively a plurality of aliquots of said particles into said corresponding plurality of additional cavity configurations within said same channel structure without the need to disassemble said channel structure;
  G. fractionating successively each said injected aliquot by means of said corresponding subsequent cavity configuration selected;
  H. measuring successively said fractionated aliquots of said particles by said detector means; and
  I. combining all such measurements collected from all aliquots so measured to provide improved characterization of said particles.

2. The method of claim 1 where each said additional cavity configuration is created by changing the effective channel length by
  A. selecting a different injection port aperture in said top plate assembly from a set of port injection means available in a row between
    a. said first cavity configuration port aperture for injecting mobile phase and
    b. said first cavity configuration port aperture for carrying said sample after fractionation to detector means; and
  B. sealing all other injection port means from said set available not selected therefrom.

3. The method of claim 1 where said additional cavity is configurations are created by replacing said spacer with a spacer containing cavities of different lengths; said cavities of said replaced spacer sharing the same mobile phase ports and sample injection ports but of different lengths associated with different fractionated sample removal ports; all ports being located in said top plate assembly of said A4F channel and all unused ports therein being made inaccessible.

4. The method of claim 1 where one or more of said additional cavity configurations are created by injecting said plurality of aliquots of said particles into alternate spacer cavities within the same spacer of said first cavity configuration, each provided with individual sets of mobile phase, sample injection, and sample removal ports; all such ports being located in said top plate assembly of said A4F channel and all unused ports therein being made inaccessible.

5. The method of claim 1 where said top plate assembly is selected from a set of such top plates, each of which provides a different set of mobile phase inflow, sample injection, and fractionated sample outflow ports to correspond to selected cavity channel structures within said spacer.

6. An improved A4F unit for the fractionation of a sample of particles suspended in fluid means comprised of
  A. a bottom plate incorporating a porous frit;
  B. a membrane permeable only to said fluid means carrying said particles suspended therein;
  C. a spacer containing two or more cavities;
  D. a top plate containing a set of associated port means providing each said cavity with
    1. a port means for injecting mobile phase fluid;
    2. a plurality of port means for injecting samples of said particles to be fractionated; each of said injection port means providing sample injection locations at different distances from said mobile phase injection port; and
    3. an exit port means for carrying said sample after fractionation to detector means.

7. The method of claim 1 further comprising the step of using said combination of said measurements to determine the effective channel length for an optimal separation of said particles.

8. The method of claim 7 where said optimal separation of said particles is that which gives a separation closest to baseline resolution.

9. The method of claim 7 where said optimal separation of said particles is that which gives most well resolved size distributions.

10. The method of claim 7 where said optimal separation of said particles is that which gives the most well resolved mass distributions.

11. The method of claim 7 where said optimal separation of said particles is that wherein the size determined by said measurement is that which is closest to the known size of said particles.

12. The method of claim 7 where said optimal separation of said particles is that wherein the mass determined by said measurement is that which is closest to the known mass of said particles.

13. The A4F system of claim 6 wherein at least one of said cavities has an effective channel length different than at least one of other said cavities.

14. The A4F system of claim 6 wherein at least one of said cavities has a different shape than at least one of other said cavities.

15. An A4F system for the fractionation of a sample of particles suspended in fluid means, comprising
   A. a top plate comprising an array of fluid ports arranged in a plurality of rows and columns extending horizontally and vertically over the accessible area of said top plate wherein each said row and column contains two or more of said fluid ports, any of which may act as a mobile phase injection port, a sample injection port, or an outflow port, as long as said sample injection port is downstream from said mobile phase injection port and upstream from said outflow port, all unused ports being made inaccessible, where the region beneath said mobile phase injection port, sample injection port, and outflow port has a properly positioned
   B. spacer containing two or more cavities separating said top plate from
   C. a membrane permeable to said fluid means lying on;
   D. a porous frit incorporated into a bottom plate; and
   E. means whereby said top plate is connected and sealed to said bottom plate.

16. The A4F system of claim 15 wherein one or more of said cavities is coffin shaped.

17. The A4F system of claim 15 wherein one or more of said cavities is not coffin shaped.

18. The A4F system of claim 15 wherein one of said cavities has an effective channel length different from the channel length of another of said cavities within said spacer.

19. The A4F system of claim 15 wherein one of said cavities has a different shape than another of said cavities within said spacer.

* * * * *